(12) United States Patent
Adachi et al.

(10) Patent No.: US 7,940,603 B2
(45) Date of Patent: May 10, 2011

(54) ULTRASONIC TRANSDUCER CELL

(75) Inventors: Hideo Adachi, Iruma (JP); Katsuhiro Wakabayashi, Hachioji (JP); Shinji Yasunaga, Asaka (JP); Mamoru Hasegawa, Nagano (JP); Kazuya Matsumoto, Nagano (JP); Ryo Ohta, Nagano (JP)

(73) Assignee: Olympus Medical Systems Corporation, Tokyo (JP)

( * ) Notice: Subject to any disclaimer, the term of this patent is extended or adjusted under 35 U.S.C. 154(b) by 23 days.

(21) Appl. No.: 11/870,827

(22) Filed: Oct. 11, 2007

(65) Prior Publication Data

US 2008/0089181 A1    Apr. 17, 2008

(30) Foreign Application Priority Data

Oct. 12, 2006 (JP) ................................. 2006-279239
Oct. 9, 2007 (JP) ................................. 2007-263695

(51) Int. Cl.
*H04R 19/00* (2006.01)

(52) U.S. Cl. ...................................................... 367/181

(58) Field of Classification Search ............ 367/87–190; 181/0.5; 310/311; 73/572
See application file for complete search history.

(56) References Cited

U.S. PATENT DOCUMENTS

| 5,287,331 | A | | 2/1994 | Schindel et al. |
| 5,652,609 | A | * | 7/1997 | Scholler et al. ................. 347/54 |
| 5,894,452 | A | * | 4/1999 | Ladabaum et al. ........... 367/163 |
| 2004/0190377 | A1 | * | 9/2004 | Lewandowski et al. ...... 367/174 |
| 2007/0057603 | A1 | * | 3/2007 | Azuma et al. ................. 310/334 |
| 2007/0164632 | A1 | * | 7/2007 | Adachi et al. ................. 310/311 |

FOREIGN PATENT DOCUMENTS

| JP | 02-052599 | | 2/1990 |
| JP | 2004-255605 | | 9/2004 |
| JP | 2006-50314 | | 2/2006 |
| WO | WO2005120130 | * | 12/2005 |

* cited by examiner

*Primary Examiner* — Thomas H Tarcza
*Assistant Examiner* — Luke D Ratcliffe
(74) *Attorney, Agent, or Firm* — Scully, Scott, Murphy & Presser, P.C.

(57) ABSTRACT

An ultrasonic transducer cell according to the present invention includes: a substrate; a charge holding portion provided on the substrate; a lower electrode provided on the charge holding portion and used to input and output a signal; and a vibration membrane provided above the lower electrode to be separated from the lower electrode with a cavity, and configured to include at least an insulating film and an upper electrode provided on the insulating film.

17 Claims, 11 Drawing Sheets

US 7,940,603 B2

ULTRASONIC TRANSDUCER CELL

CROSS REFERENCE TO RELATED APPLICATION

This Application claims benefit of Japanese Applications No. 2006-279239 filed on Oct. 12, 2006 and No. 2007-263695 filed on Oct. 9, 2007 the contents of which are incorporated by this reference.

BACKGROUND OF THE INVENTION

1. Field of the Invention

The present invention relates to a capacitive ultrasonic transducer cell.

2. Description of the Related Art

The ultrasonic transducer cell has a function of converting an electric signal into an ultrasound and transmitting the ultrasound to an object, or a function of receiving the ultrasound reflected by the object and converting the received ultrasound into an electric signal.

More specifically, the ultrasonic transducer cell is configured by including a pair of plate-like electrodes (parallel plate electrodes) arranged opposite to each other so as to sandwich a cavity. Further, one of the pair of electrodes is included in a vibration membrane, so that an ultrasound is transmitted and received by vibration of the vibration membrane. When receiving an ultrasound, the ultrasonic transducer cell converts the ultrasonic signal into an electric signal on the basis of a change in the electrostatic capacitance between the pair of electrodes. Thus, in the case of an ultrasonic transducer cell of a conventional type, it is necessary to apply a DC bias voltage to the pair of electrodes especially at the time of reception.

In Japanese Patent Laid-Open No. 2-52599, there is disclosed an ultrasonic transducer cell which eliminates the need to apply the DC bias voltage by providing an electret membrane between the pair of electrodes.

The sound pressure of an ultrasound transmitted by the ultrasonic transducer cell depends on the electrostatic capacitance between the pair electrodes. FIG. 17 shows an equivalent circuit diagram of the ultrasonic transducer cell disclosed in Japanese Patent Laid-Open No. 2-52599. The ultrasonic transducer cell disclosed in Japanese Patent Laid-Open No. 2-52599 is configured by providing an electret film 503 between a pair of electrodes 501 and 502. In this case, the composite electrostatic capacitance C1 between the pair of electrodes 501 and 502 becomes a value obtained by combining an electrostatic capacitance Cmem of an insulating film 506, an electrostatic capacitance Ccav of a cavity 504 and an electrostatic capacitance Cele of the electret film 503.

Here, the thickness of the cavity 504 is determined by a thickness required for the insulating film 506, and hence is fixed regardless of the presence of the electret film 503. For this reason, the composite electrostatic capacitance C0 between the electrodes 501 and 502 at the time when the electret film 503 is not provided between the electrodes 501 and 502, is larger than the composite electrostatic capacitance C1.

In other words, in the configuration of the conventional ultrasonic transducer cell, it is not possible to maintain the electrostatic capacitance while reducing the DC bias voltage.

SUMMARY OF THE INVENTION

An ultrasonic transducer cell according to the present invention includes: a substrate; a charge holding portion provided on the substrate; a lower electrode provided on the charge holding portion and used to input and output a signal; and a vibration membrane provided above the lower electrode to be separated from the lower electrode with a cavity, and configured to include at least an insulating film and an upper electrode provided on the insulating film.

The above and other objects, features and advantages of the invention will become more clearly understood from the following description referring to the accompanying drawings.

DETAILED DESCRIPTION OF THE PREFERRED EMBODIMENTS

An ultrasonic transducer cell according to the present invention includes: a substrate; a charge holding portion provided on the substrate; a lower electrode provided on the charge holding portion and used to input and output a signal; and a vibration membrane provided above the lower electrode to be separated from the lower electrode with a cavity and configured to include at least an insulating film and an upper electrode arranged on the insulating film. The ultrasonic transducer cell according to the present invention, having the above described configuration, is capable of reducing the DC bias voltage or eliminating the need of the DC bias voltage while suppressing the lowering of the electrostatic capacitance.

The application of the ultrasonic transducer cell according to the present invention is not limited in particular, but for example, the ultrasonic transducer cell can be used for an ultrasonic endoscope. In the following, there will be described an example of an ultrasonic endoscope to which the ultrasonic transducer cell according to the present invention can be applied. However, the ultrasonic endoscope to which the ultrasonic transducer cell according to the present invention is applied, is not limited to the following description, and the ultrasonic transducer cell according to the present invention can be applied to a conventionally known endoscope. For example, the ultrasonic transducer cell according to the present invention may be applied to an ultrasonic endoscope of an ultrasonic probe type, or an ultrasonic endoscope of a capsule type.

Figure 1:
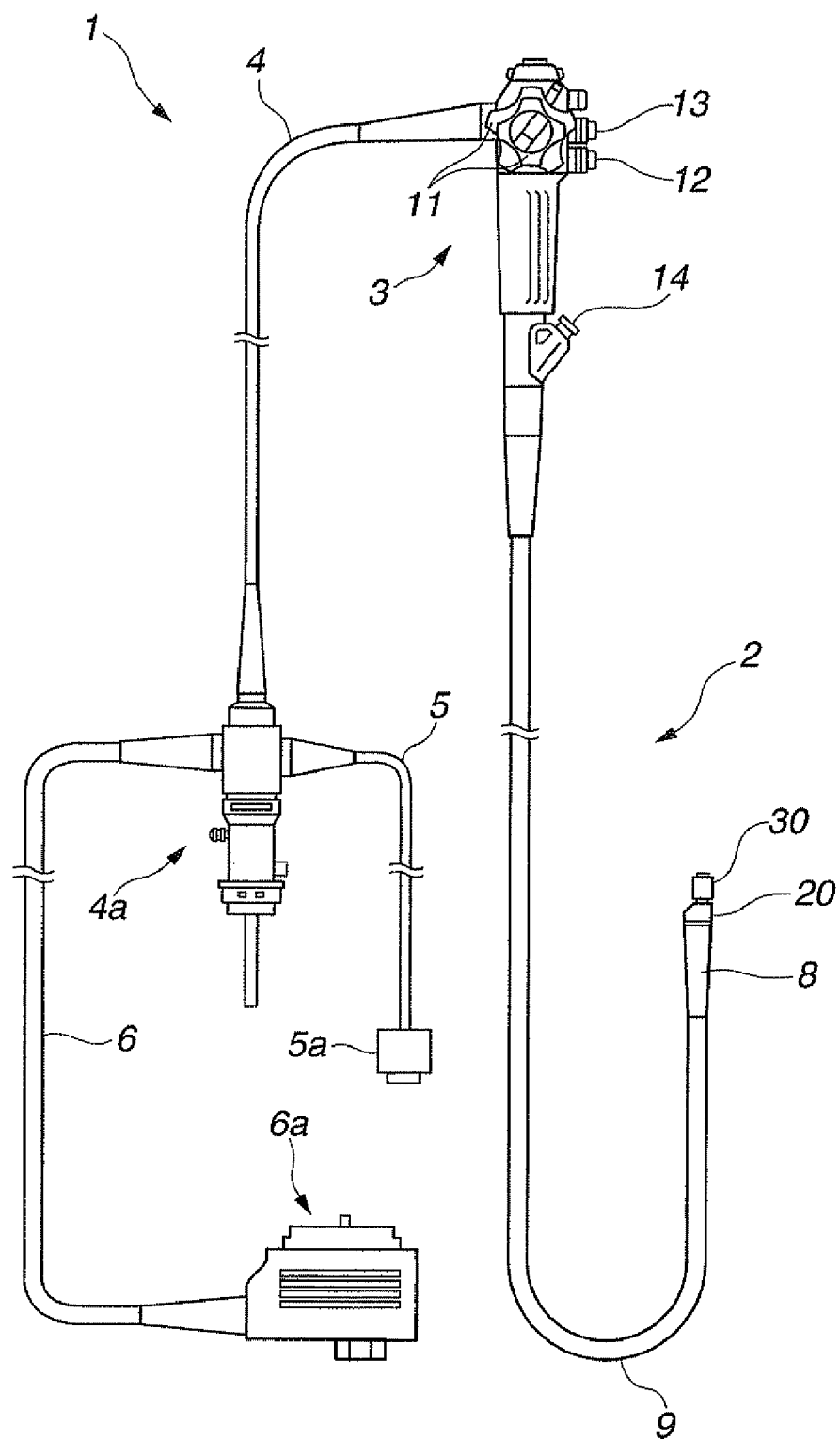
FIG. 1 is an illustration showing a schematic configuration of an ultrasonic endoscope.
Figure 2:
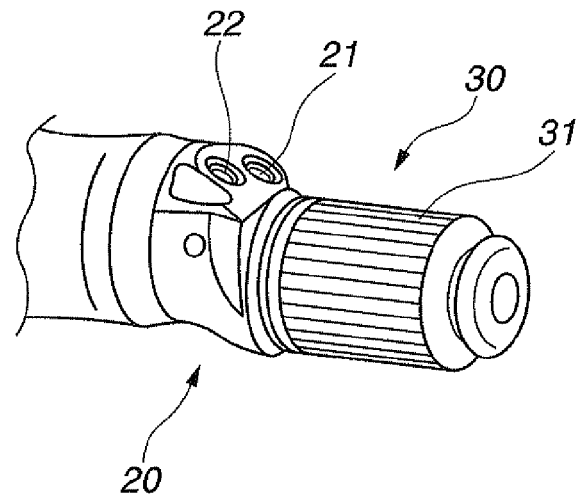
FIG. 2 is a perspective view showing a configuration of a distal end portion of the ultrasonic endoscope.
Figure 3:
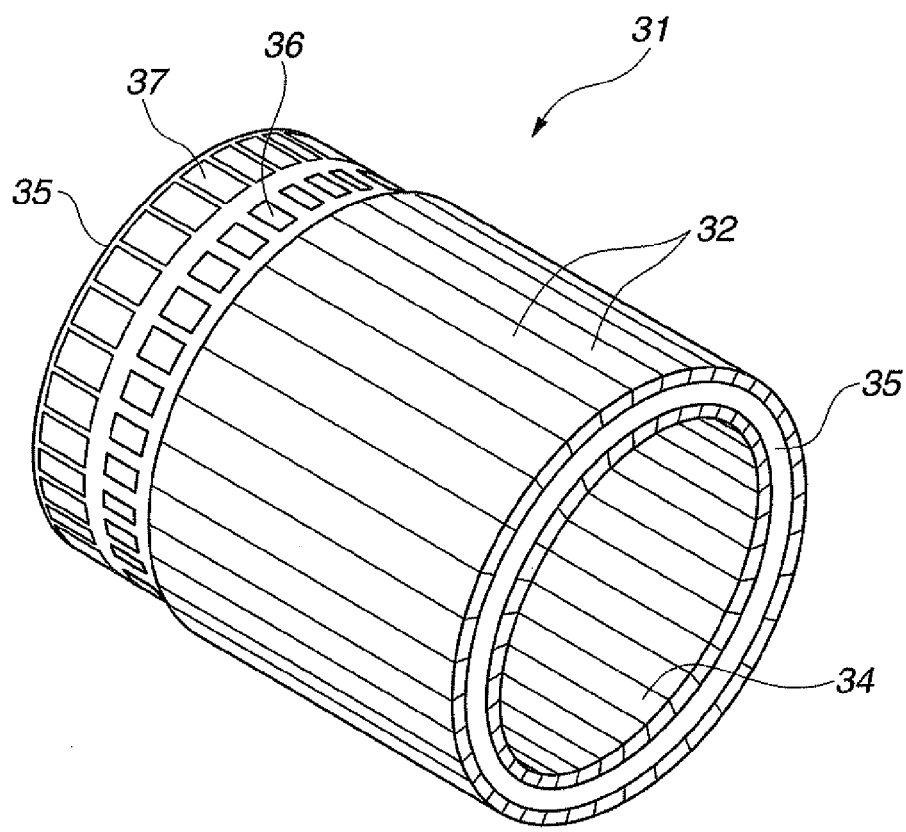
FIG. 3 is a perspective view showing an ultrasonic transducer array.
Figure 4:
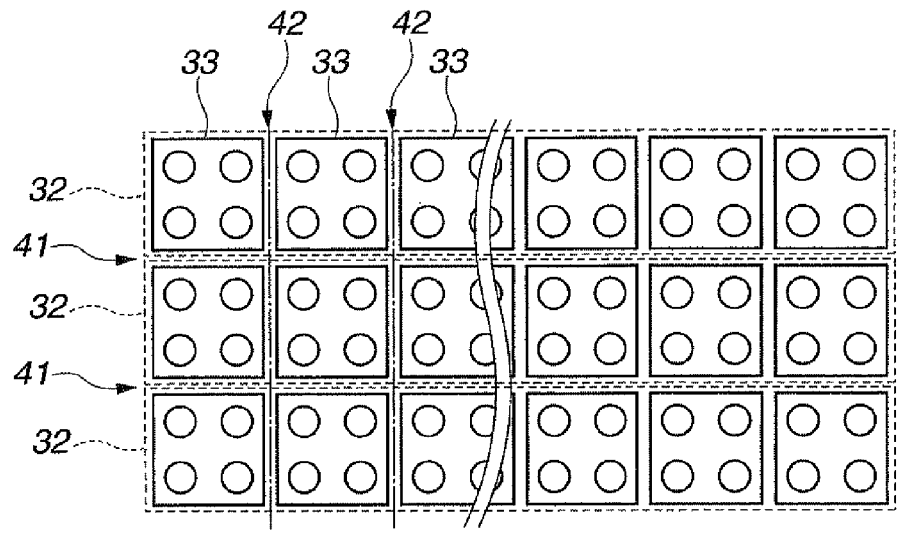
FIG. 4 is a top view of an ultrasonic transducer unit as viewed from the transmitting and receiving direction of ultrasounds.

In the following, there will be described an example with reference to FIG. 1 to FIG. 8. Note that as for the shape of respective components, the ratio between the sizes of the respective components, the arrangement position of the respective components, or the like, the present invention is not limited only to those shown in the figures. FIG. 1 is an illustration showing a schematic configuration of an ultrasonic endoscope. FIG. 2 is a perspective view showing a configuration of a distal end portion of the ultrasonic endoscope. FIG. 3 is a perspective view showing an ultrasonic transducer array. FIG. 4 is a top view of an ultrasonic transducer unit as viewed from the transmitting and receiving direction of ultrasounds.

As shown in FIG. 1, an ultrasonic endoscope 1 can be mainly configured by a slim and long insertion portion 2 introduced into the inside of a body, an operation portion 3 positioned at a proximal end of the insertion portion 2, and a universal cord 4 configured to extend from the side portion of the operation portion 3.

For example, an endoscope connector 4a connected to a light source (not shown) may also be provided in the proximal end portion of the universal cord 4. From the endoscope connector 4a, it is possible to extend an electric cable 5 attachably and detachably connected to a camera control unit (not shown) via an electric connector 5a, and to extend an ultrasonic cable 6 attachably and detachably connected to an ultrasonic observation apparatus (not shown) via an ultrasonic connector 6a.

For example, the insertion portion 2 is configured by providing successively from the distal end side, a distal end rigid portion 20, a flexible bending portion 8 positioned at the rear end of the distal end rigid portion 20, and a flexible tube portion 9 which is positioned at the rear end of the bending portion 8 to reach the distal end of the operation portion 3 and has a small diameter and a long length. Further, an ultrasonic transmission and reception portion 30 for transmitting and receiving ultrasounds as will be described in detail below is provided on the distal end side of the distal end rigid portion 20. A material forming the distal end rigid portion is not limited in particular, but a resin and the like is listed as the material.

In the operation portion 3, it is possible to provide an angle knob 11 adapted to control the bending of the bending portion 8 in a desired direction, an air supply and water supply button 12 for performing air supply and water supply operations, a suction button 13 for performing a suction operation, a treatment tool insertion port 14 serving as an inlet of a treatment tool introduced into the inside of the body, and the like. As shown in FIG. 2, there may be provided in the distal end rigid portion 20 an illumination lens (not shown) configuring an illumination optical portion for irradiating an observation site with illumination light, an objective lens 21 configuring an observation optical portion for capturing an optical image of the observation site, a suction and forceps port 22 serving as an opening through which an excised part is sucked and a treatment tool is projected, and an air supply and water supply port (not shown) for supplying the air and the water. However, the distal end rigid portion to which the ultrasonic transducer cell according to the present invention is applied, is not limited to the above described configuration, and the ultrasonic transducer cell according to the present invention can be applied to a conventionally known configuration.

The ultrasonic transmission and reception portion 30 provided at the distal end of the distal end rigid portion 20 may be configured by including an ultrasonic transducer array 31, a drive circuit 34, and an FPC 35, as shown in FIG. 3. The FPC 35 is a flexible wiring substrate having mounting surfaces formed on both surfaces thereof. In the ultrasonic transmission and reception portion 30, the FPC 35 is preferably provided by being wound in a substantially cylindrical shape around an axis, as a central axis, which is substantially in parallel with the insertion axis of the distal end rigid portion 20. It is preferred that the wiring substrate is a flexible printed wiring circuit board.

In the example shown in FIG. 3, the ultrasonic transducer array 31 which is a two-dimensional ultrasonic transducer array is provided on the outer peripheral surface of the cylindrical FPC 35. The ultrasonic transducer array 31 is configured by including a plurality of ultrasonic transducer units 32 arranged on the outer peripheral surface and in the peripheral direction of the FPC 35. The ultrasonic transducer units 32, each of which has an approximately rectangular shape when viewed from the normal direction of the outer peripheral surface of the FPC 35, are arranged at equal intervals on the outer peripheral surface of the cylindrical FPC 35 by taking the short direction of the ultrasonic transducer unit as the peripheral direction. The number of the ultrasonic transducer units 32 configuring the ultrasonic transducer array 31 is not limited in particular. However, it is possible to configure the ultrasonic transducer array 31 by, for example, several tens to several hundreds of the ultrasonic transducer units 32. For example, the numbers, such as 16, 32, 48, 64, 128, 192, or 256, can be selected depending on the purpose. The ultrasonic transducer array 31 shown in FIG. 3 includes 36 number of the ultrasonic transducer units 32.

Further, the ultrasonic transducer unit 32 may be configured in such a manner that a plurality of ultrasonic transducer elements 33 are arranged as illustrated in FIG. 4. However, the arrangement position, the number of arrangement, or the like, of the ultrasonic transducer elements is not limited only to that as illustrated in FIG. 4. In FIG. 4, the ultrasonic transducer elements 33, each of which has a square shape when viewed from the normal direction of the outer peripheral surface of the FPC 35, are one-dimensionally arranged in the longitudinal direction of the ultrasonic transducer unit. In the present invention, the number of the ultrasonic transducer units is not limited in particular, and it is possible to select the number, such as 36, 48 or 64, depending on the purpose.

Figure 5:
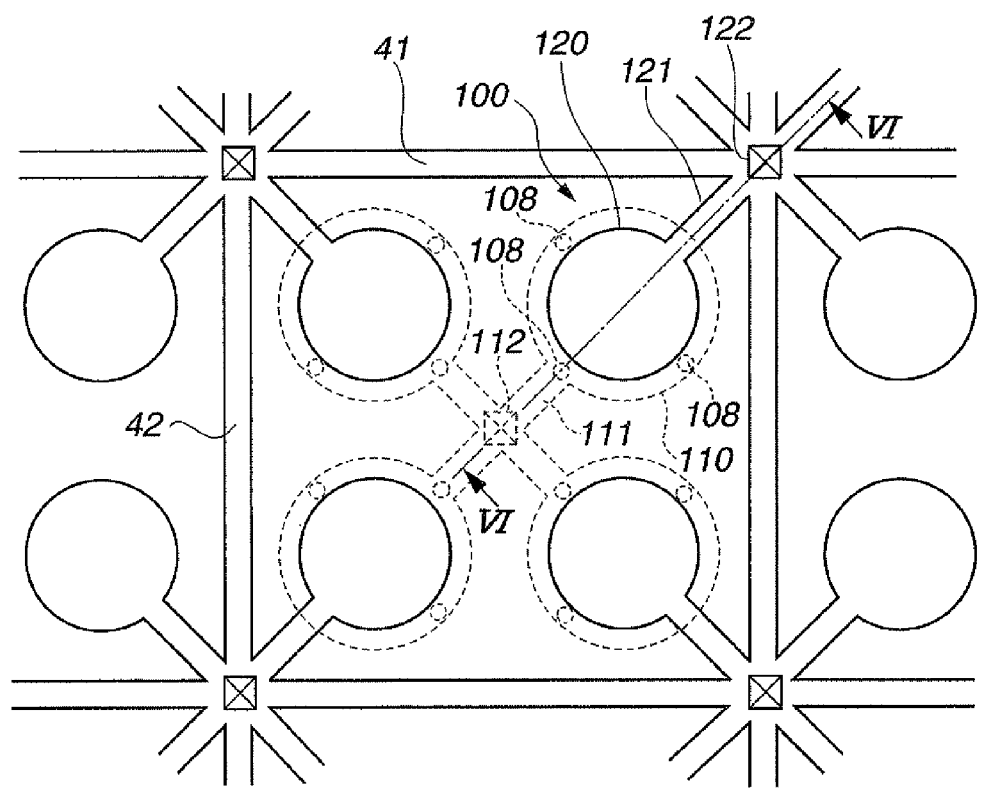
FIG. 5 is a top view of an ultrasonic transducer cell.

The ultrasonic transducer element 33 is configured by a plurality of ultrasonic transducer cells 100 as will be described in detail below. In the same ultrasonic transducer element 33, it is preferred that the ultrasonic transducer cells 100 are all electrically connected in parallel with each other. Thereby, the ultrasonic transducer element 33 is capable of simultaneously transmitting ultrasounds in the same phase with each other, when receiving a drive signal from an ultrasonic observation apparatus. That is, in the present embodiment, one ultrasonic transducer element 33 configures a minimum drive unit for transmitting and receiving ultrasounds. In FIG. 4 and FIG. 5, the ultrasonic transducer element 33 is configured by four ultrasonic transducer cells 100.

As illustrated in FIG. 4 and FIG. 5, between the ultrasonic transducer units 32 adjacent to each other, it is possible to form an ultrasonic transducer unit boundary groove 41 which is a groove portion serving to define each of the ultrasonic transducer units 32. However, the shape of the boundary groove is not limited only to the shape shown in FIG. 4 or FIG. 5. Further, also between the ultrasonic transducer elements 33, it is possible to form an ultrasonic transducer element boundary groove 42 which is a groove portion serving to define each of the ultrasonic transducer elements 33. In this way, by providing the groove portion in the outer circumference of the ultrasonic transducer element 33 as the minimum drive unit, it is possible to reduce the cross talk between the ultrasonic transducer elements 33 adjacent to each other.

The ultrasonic transducer element 33 transmits ultrasounds in the normal direction of the mounting surface of the FPC 35, that is, outward in the radial direction of the cylindrical FPC 35. Therefore, the ultrasonic transducer unit 32 configured by one-dimensionally arranging the ultrasonic transducer elements 33 configures a one-dimensional ultrasonic transducer array. The ultrasonic transducer array 31 which is a two-dimensional ultrasonic transducer array is configured by arranging the plurality of ultrasonic transducer units 32.

On the other hand, it is possible to mount the plurality of drive circuits 34 on the inner peripheral surface of the cylindrical FPC 35, that is, on the mounting surface opposite the mounting surface on which the ultrasonic transducer array 31 is mounted. The drive circuit 34 has electronic circuits, such as a pulsar for driving the ultrasonic transducer element 33 and a selection circuit, and can be electrically connected to each of the ultrasonic transducer elements 33.

Further, the drive circuit 34 can be electrically connected to a plurality of signal electrodes 36 and grounding electrodes 37 which are formed on the outer peripheral surface of the cylindrical FPC 35. Note that although the signal electrode 36 is shown by one electrode in FIG. 3, the signal electrode 36 is divided in correspondence with the number of the ultrasonic transducer elements 33, and hence the one signal electrode 36 can be provided for the one ultrasonic transducer element 33.

The signal electrode 36 and the grounding electrode 37 are electrically connected to terminals at one end of a coaxial cable which is inserted through the inside of the ultrasonic cable 6 so as to be electrically connected to the ultrasonic connector 6a at terminals at the other end of the coaxial cable. Therefore, the drive circuit 34 is electrically connected to the ultrasonic observation apparatus.

The ultrasonic transmission and reception portion 30 having the above described configuration is capable of simultaneously or alternately performing a so-called electronic radial scanning for radially transmitting and receiving ultrasounds on a plane orthogonal to the insertion axis of the distal end rigid portion 20, and a so-called electronic sector scanning for radially transmitting and receiving ultrasounds on a plane including the insertion axis of the distal end rigid portion 20, by means of the ultrasonic transducer array 31 which is a two-dimensional ultrasonic transducer array provided on the outer peripheral surface of the cylindrical FPC 35. That is, the above described ultrasonic endoscope 1 is capable of performing a three-dimensional ultrasonic scanning in the inside of the body.

In the following, preferred embodiments of the ultrasonic transducer cell according to the present invention will be described. However, the present invention is not limited only to the following embodiments.

First Embodiment

Figure 6:
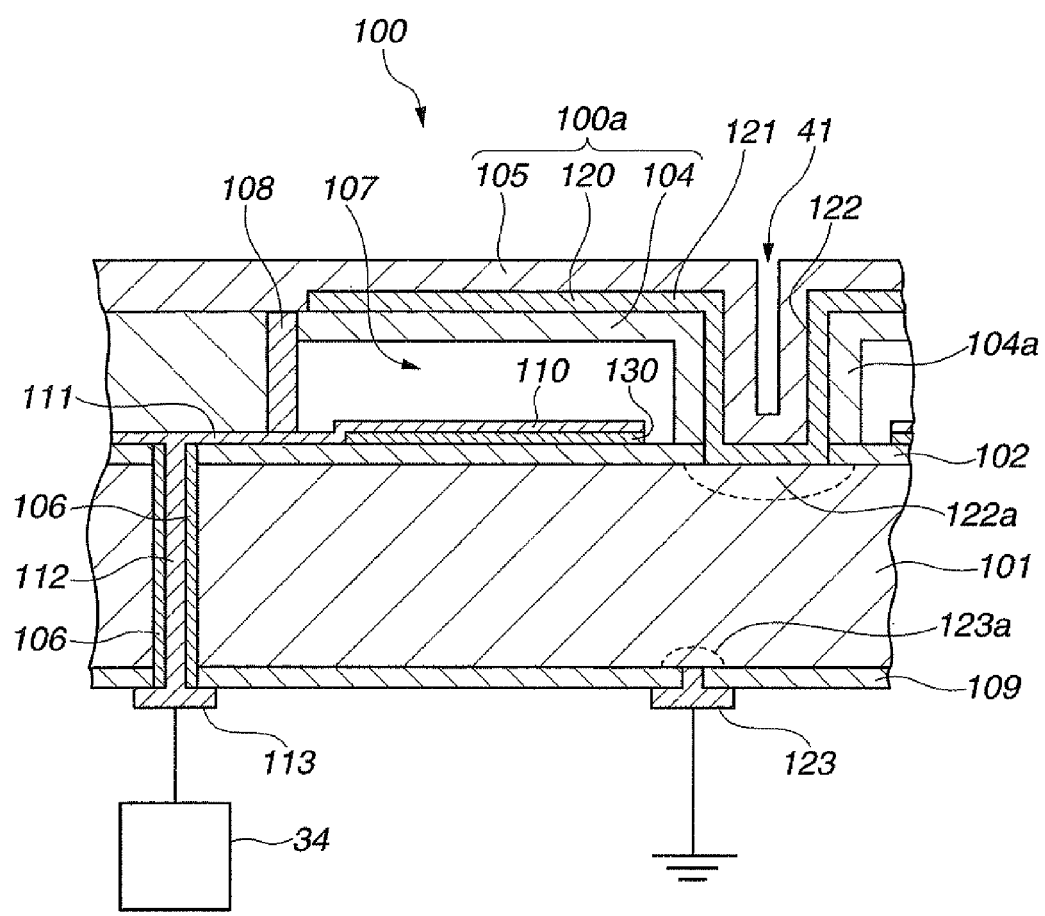
FIG. 6 is a cross-sectional view along the line VI-VI in FIG. 5.
Figure 7:
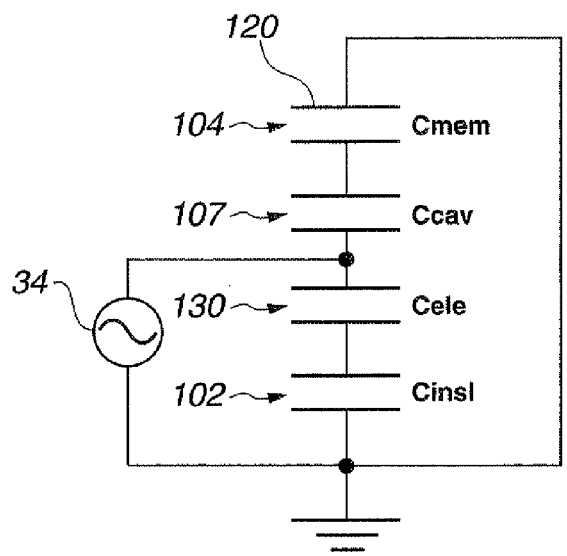
FIG. 7 is an equivalent circuit diagram of the ultrasonic transducer cell.

FIG. 5 is a top view of the ultrasonic transducer cell 100. FIG. 6 is a cross-sectional view along the line VI-VI in FIG. 5. FIG. 7 is an equivalent circuit diagram of the ultrasonic transducer cell 100.

Note that in the following description of a layered configuration, it is assumed that as for the upper and lower relation between respective layers, the direction away from the surface of the substrate 101 in the normal direction is the upper direction. For example, in the cross-sectional view of FIG. 6, it is referred that an upper electrode 120 is arranged above a lower electrode 110. Further, the thickness of each layer means a dimension of the each layer in the direction parallel to the normal of the substrate 101 surface. Furthers in the following description, for convenience, among the surfaces of the substrate 101, the surface on which the ultrasonic transducer cells 100 are formed is referred to as a cell forming surface, and the surface opposite the surface on which the ultrasonic transducer cells 100 are formed is referred to as a rear surface.

The ultrasonic transducer cell 100 is configured by including the lower electrode 110 (a first electrode) and the upper electrode 120 (a second electrode) which are a pair of parallel plate electrodes facing each other via a cavity 107. The ultrasonic transducer cell 100 transmits and receives ultrasounds by the vibration of a vibration membrane 110a which is an elastic film-like configuration body including the upper electrode.

The configuration of the ultrasonic transducer cell 100 according to the present embodiment will be described in detail below.

The material of a substrate 101 included in the ultrasonic transducer cell according to the present invention is not limited in particular, and for example, the ultrasonic transducer cell may be configured by a conductive material or an insulating material. In the following, a substrate configured by a conductive material is also described as a conductive substrate, and a substrate configured by an electrically insulating material is also described as an insulating substrate.

In the case where the substrate is the conductive substrate, the material configuring the substrate is not limited in particular, and hence a conventionally known conductive material can be used. For example, a conductive material, such as a silicon semiconductor, can be used.

In the case where the substrate is the conductive substrate, it is also possible to arrange an insulating film on the surface of the substrate, on which surface the charge holding portion is not formed, or on both surfaces of the substrate. In the present invention, an insulating film arranged on the side of the charge holding portion of the substrate surfaces is described as a first insulating film, and an insulating film arranged on the other surface of the substrate surfaces is described as a rear surface insulating film. The method for arranging the insulating films is not limited in particular, but for example, it is possible to arrange a first insulating film 102 and a rear surface insulating film 109 in a manner as denoted by reference numerals 102 and 109 in FIG. 6. The material of the first insulating film and the rear surface insulating film is not limited in particular, and it is possible to use, as the material, a conventionally known insulating material. For example, it is possible to use, as the material, an insulating material, such as a silicon oxide, quartz, sapphire, crystal, alumina, zirconia, glass, or a resin. When a silicon semiconductor is used as the substrate 101, and when a silicon oxide is used as the first insulating film 102 and the rear surface insulating film 109, the silicon oxide film can be formed on both sides of the silicon substrate 101 by subjecting the silicon substrate 101 to the thermal oxidation processing.

When the substrate is an insulating substrate, the material configuring the insulating substrate is not limited in particular, and it is possible to use, as the material, a conventionally known insulating material. For example, it is possible to use an insulating material, such as a silicon oxide, a silicon nitride, quartz, sapphire, crystal, alumina ceramics, zirconia ceramics, glass, or a resin.

The shape or the thickness of the substrate 101 is not limited in particular, and it is possible to appropriately select a suitable shape depending on the purpose.

The charge holding portion for holding electric charges is formed on a cell forming surface on the substrate 101, that is, on the first insulating film 102. The shape of the charge holding portion is not limited in particular, but is preferably a circular shape.

The charge holding portion is not limited in particular, but is preferably an electret film including an electret.

In the present invention, the method for forming the electret film is not limited in particular. For example, it is possible to form the electret film in such a manner that a silicon oxide film formed by a plasma CVD method or the like is charged by corona discharge.

Note that when the electret film is used as the charge holding portion 130, the electret film may be configured by a silicon compound such as $SiO_2$ or SiN, or a hafnium oxide such as $HfO_2$ or $HfAl_2O_5$. These compounds and oxides are excellent in insulating property. It is possible to fix the charges in a trap of a deep level of the electret film by using a highly insulating silicon compound and hafnium oxide as the electret film. This makes it possible to obtain an electric potential stabilized over the long period of time.

Figure 8:
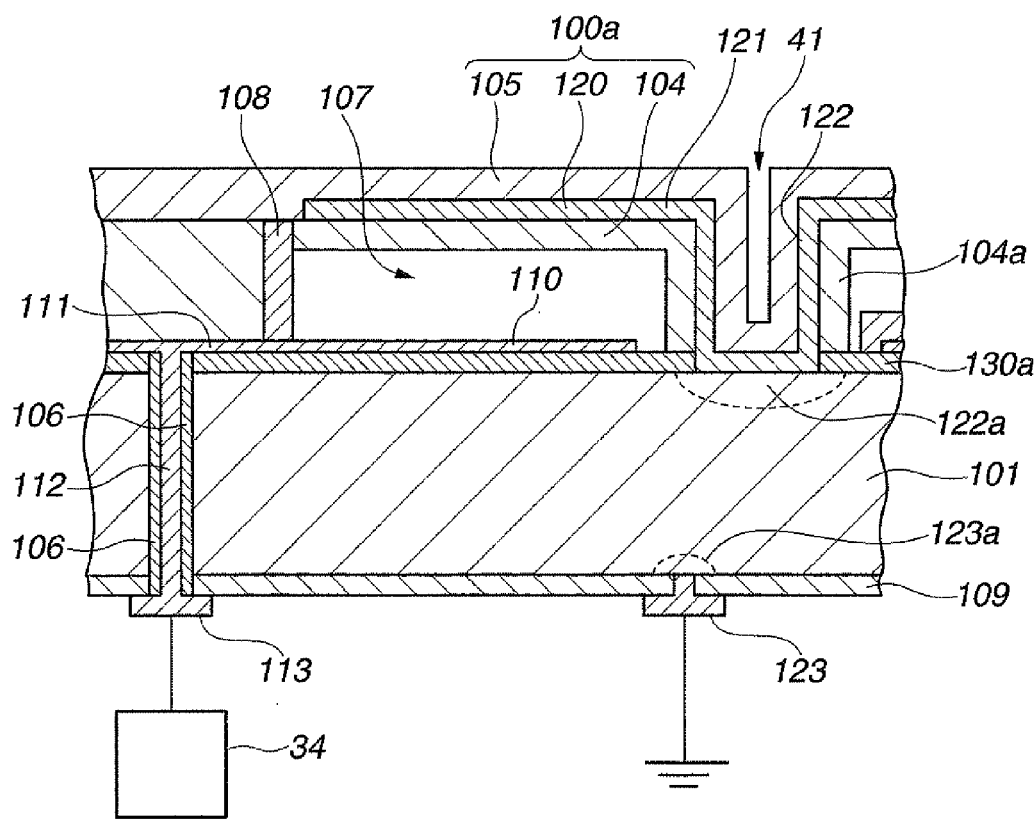
FIG. 8 is a partial cross-sectional view showing a modification of the ultrasonic transducer cell according to the first embodiment.

When the electret film is used as the charge holding portion, and when the charge holding portion 130a is directly formed on the conductive substrate 101 as illustrated in FIG. 8, the charges are held near the boundary surface between the charge holding portion 130a and the substrate 101. This makes it possible to stably hold the charges.

The lower electrode 110 is formed on the charge holding portion 130. The shape of the lower electrode is not limited in particular, but is preferably the same shape as that of the charge holding portion 130. More preferably, the shape is a circular shape.

The method for forming the lower electrode 110 is not limited in particular. For example, it is possible to form the lower electrode 110 by patterning a film formed by sputtering.

The material of the lower electrode 110 is not limited in particular, but it is preferred to use, as the material, aluminum, copper, molybdenum, tungsten, titanium, tantalum, or an alloy of these materials. Among these materials, aluminum or copper has an advantage of being excellent in the cost performance, while tungsten, titanium, tantalum, or an alloy of these materials are high-melting-point metals, and hence have an advantage that a high temperature process can be adopted in the manufacturing process of the ultrasonic transducer cell.

In the following, arrangement positions and components included in an ultrasonic transducer element will be described in conjunction with the description of Embodiment 1, in the case where the ultrasonic transducer cell according to Embodiment 1 is applied to the ultrasonic transducer element. However, the present invention is not limited to the following description.

As illustrated in FIG. 6, the lower electrode 110 may be electrically connected to a signal electrode pad 113 for receiving an external electric signal and transmitting an electric signal from the lower electrode through a lower electrode wiring 111. In FIG. 5, adjacent four electrodes of the lower electrode 110 are electrically connected to each other by the lower electrode wiring 111 having an X shape when viewed from the above.

A wafer through-electrode 112 formed to pass through the substrate 101 is provided, for each unit of the ultrasonic transducer element 33, at the crossing portion of the lower electrode wiring 111 having the X shape when viewed from the above. The wafer through-electrode 112 may be electrically connected to the signal electrode pad 113 which is electrically insulated from the substrate 101 by an insulating portion 106 and formed on the rear surface insulating film 109. That is, the lower electrode 110 may be electrically connected to the signal electrode pad 113 formed on the rear surface of the substrate 101 via the lower electrode wiring 111 and the wafer through-electrode 112.

The vibration membrane 100a is arranged across the cavity 107 on the lower electrode 110. The vibration membrane includes at least a second insulating film 104 and the upper electrode 120 arranged on the second insulating film 104, but may also include an upper electrode protective film 105 as illustrated in FIG. 6. In the following, the insulating film included in the vibration membrane will also be described as a second insulating film in order to be distinguished from the above described insulating film formed on the surface of the substrate 101.

The material configuring the second insulating film 104 is not limited in particular, and it is possible to use a conventionally known electrically insulating material. As the materials) there are listed such insulating materials as, for example, a silicon oxide, a silicon nitride, quartz, sapphire, crystal, alumina, zirconia, glass, or a resin. The method for manufacturing the second insulating film 104 is not limited in particular, and it is possible to manufacture the second insulating film 104, for example, by an LPCVD method or a plasma CVD method.

As described above, a cavity is arranged between the lower electrode 110 and the vibration membrane 100a. The internal pressure of the cavity is not limited in particular, and may be set to the atmospheric pressure. The internal pressure of the cavity may also be in a depressurized state or in a vacuum state.

The shape of the cavity is not limited in particular, and is suitably determined by the wavelength and output of the ultrasound used at the time of observation. For example, the shape of the cavity may be a cylindrical shape, a hexagonal shape, a square pole shape or the like.

The method for forming the cavity 107 is not limited in particular, and it is possible to form the cavity 107 by sacrificial layer etching as a conventionally known technique. When the sacrificial layer etching is used, a sacrificial layer removing hole for communicating the inside of the cavity 107 with the upper layer of the second insulating film 104 is formed. However, it is preferred that the sacrificial layer removing hole is sealed by a plug 108 as illustrated in FIG. 6. The forming number and the forming positions of the sacrificial layer removing holes are not limited in particular, and can be suitably determined depending on the shape of the cavity or the like. For example, in FIG. 5, the sacrificial layer removing holes are formed at three positions of the outer peripheral part of the cavity 107. Note that the cavity 107 may be formed by a method for joining the wafers subjected to microfabrication.

It is preferred that the upper electrode 120 is provided concentrically with the lower electrode 110, that is, provided at the position so as to face the lower electrode 110 when viewed from the above.

The method for forming the upper electrode 120 is not limited in particular, and it is possible to form the upper electrode 120, for example, by patterning a film formed by sputtering.

The adjacent four electrodes in the upper electrode 120 can be electrically connected to each other by an upper electrode wiring 121 having an X shape when viewed from the above. Here, it is preferred that the upper electrode wiring 121 is arranged so that a part of the upper electrode wiring 121 overlapping the above described lower electrode wiring 111 is minimized when viewed from the above. In this way, the lower electrode wiring 111 and the upper electrode wiring 121 are arranged so as to minimize the overlapping portion between the wirings, whereby it is possible to prevent the parasitic capacitance in the wiring portion from being generated.

The material configuring the upper electrode is not limited in particular, and it is possible to use a conventionally known conductive material. For example, it is possible to use such conductive material as Al, Cu, W, Mo, Ti or Ta as the material configuring the upper electrode. Further, the upper electrode 120 may be made of only one kind of conductive material, or may have a multilayer configuration formed by layering a plurality of kinds of conductive materials.

As illustrated in FIG. 5 and FIG. 6, it is preferred that the crossing portion of the upper electrode wiring 121 having the X shape when viewed from the above is formed on the ultrasonic transducer unit boundary groove 41. It is preferred that the ultrasonic transducer unit boundary groove 41 is formed in a depth to reach the substrate 101 through a vibration membrane supporting section 104a of the second insulating film 104. A through-electrode 122 is film-formed in the ultrasonic transducer unit boundary groove 41 by the same process as the upper electrode 120 and the upper electrode wiring 121. It is preferred that the through-electrode 122 is electrically connected to the substrate 101 via an ohmic contact region 122a.

Further, a grounding electrode pad 123 is formed on the rear surface insulating film 109. It is preferred that the grounding electrode pad 123 is electrically connected to the substrate 101 via an ohmic contact region 123a. That is, it is preferred that the upper electrode 120 is electrically connected to the grounding electrode pad 123 formed on the rear surface of the substrate 111 via the upper electrode wiring 121, the through-electrode 122 and the substrate 101.

The method for forming the upper protective film 105 is not limited in particular, and it is possible to form the upper protective film 105, for example, by the plasma CVD method.

The material configuring the upper protective film 105 is not limited in particular, and the upper protective film may be configured, for example, by silicon nitride, a silicon oxide film, hafnium nitride (HfN), hafnium oxynitride (HfON) or the like. Particularly, it is possible to obtain a high-density film by HfN or HfON, and hence the materials are preferably used for the protective film.

Further, although not shown, a film which has water resistance, chemical resistance and the like, and which is excellent in biocompatibility and electrical insulating property may also be formed on the upper protective film 105. More specifically, a film made of a paraxylene resin may be formed on the upper protective film 105.

The method for forming the above described ultrasonic transducer cell is not limited in particular, and it is possible to form the ultrasonic transducer cell, for example, by using a MEMS (Micro Electro Mechanical Systems) process. The ultrasonic transducer formed by the MEMS process is generally referred to as c-MUT (Capacitive Micromachined Ultrasonic Transducer). When the MEMS process is utilized, it is possible to form the ultrasonic transducer cell or the ultrasonic transducer element without using lead.

It is preferred that the ultrasonic transducer element 31 with the ultrasonic transducer cell 100 having the above described configuration is mounted on the FPC 35 by a conventionally known method, such as for example, a solder bonding, an anisotropic conductive film bonding, and an ultrasonic bonding. It is preferred that the ultrasonic transducer cell 100 is electrically connected to the drive circuit 34 mounted on the opposite side of the FPC 35 via the signal electrode pad 113 and the grounding electrode pad 123.

That is, it is preferred that transmission and reception of a drive signal and a reception signal, which are voltage signals, are performed between the lower electrode 110 and the drive circuit 34 via the signal electrode pad 113. Further, it is preferred that the grounding electrode pad 123 is set to the ground potential, and the upper electrode 120 is connected to the ground potential via the substrate 101 and the grounding electrode pad 123.

In this way, the substrate 101 included in the ultrasonic transducer cell 100 is formed by a conductive silicon and set to the ground potential, whereby it is possible to shield the noise entering from the rear surface side and to obtain an ultrasonic image with a higher S/N ratio.

Further, the signal electrode pad 113 and the grounding electrode pad 123 are provided on the rear surface side of the ultrasonic transducer cell 100, whereby it is possible to reduce the mounting area.

In the ultrasonic transducer cell 100 having the above described configuration, a potential difference is always generated between the pair of electrodes of the lower electrode 110 and the upper electrode 120 by the charges held in the charge holding portion 130 electrically connected in series to the lower electrode 110. That is, the ultrasonic transducer cell 100 is set to a state electrically equivalent to the state where a DC bias voltage is applied between the lower electrode 110 and the upper electrode 120. This enables the ultrasonic transducer cell 100 to transmit and receive ultrasounds under the application of a DC bias voltage lower than the conventional DC bias voltage or without the external application of the DC bias voltage. That is, it is possible to lower the voltage effective value of the signal for driving the ultrasonic transducer cell 100. Therefore, it is possible to eliminate the need of the circuit and wiring for applying the DC bias voltage which are necessary in the conventional ultrasonic transducer cell, and to thereby miniaturize the device.

Further, according to the present embodiment, since the voltage effective value of the drive signal is suppressed to be low, the value of current flowing through the drive circuit or the wiring is reduced, so that the power consumption can be lowered. This makes it possible to further reduce the size of the drive circuit and to prevent the characteristic of the ultrasonic transducer cell from being changed by the heat generation of the drive circuit.

Further, the composite capacitance $C_t$ between the lower electrode 110 and the upper electrode 120 of the ultrasonic transducer cell 100 having the above described configuration becomes a capacitance obtained by serially connecting the capacitance $C_{mem}$ of the second insulating film 104 and the capacitance $C_{cav}$ of the cavity 107, as shown in FIG. 7.

That is, in the present embodiment, since it is not necessary to provide the charge holding portion 130 between the lower electrode 110 and the upper electrode 120, it is possible to prevent the distance between the lower electrode 110 and the upper electrode 120 from being increased as before by providing the charge holding portion 130 between the electrodes, thereby suppressing lowering of the capacitance between the electrodes.

Therefore, according to the present embodiment, it is possible to increase the capacitance between the mutually opposing electrodes and to obtain a higher sound pressure of transmitted ultrasounds, as compared with conventional ones. Thus, it is possible to obtain an ultrasonic transducer cell having high sensitivity.

As described above, according to the present embodiment, it is possible to transmit and receive ultrasounds with a reduced DC bias voltage or without application of the DC bias voltage, and to obtain an ultrasonic transducer cell having high sensitivity.

Further, in the case of the above described configuration, the drive signal for driving the ultrasonic transducer cell 100 is applied to the lower layer side of the ultrasonic transducer cell 100, that is, to the lower electrode 110 positioned on the side opposite the direction for transmitting and receiving the ultrasounds to and from the observation object. Here, the upper electrode 120 provided at the position nearer to the observation object as compared with the lower electrode 110 is connected to the ground potential. That is, only the conductive layer connected to the ground potential is provided in the outer peripheral portion of the ultrasonic transducer cell 100 according to the present embodiment, while the conductive layer to which the drive signal is applied is provided only in the inside of the ultrasonic transducer cell 100. Therefore, it is possible to surely and easily secure the electrical insulation between the conductive layer to which the drive signal is applied, and the outside. In addition, as described above, the wiring or the like for applying the DC bias voltage of a high effective value is not necessary depending on an ultrasonic transducer cell. Thus, for example, it is possible to reduce the thickness of the protective film for covering the ultrasonic transducer cell 100 and to thereby miniaturize the device.

Further, according to the ultrasonic endoscope 1 including the ultrasonic transducer cell 100 of the present embodiment, it is possible to obtain an ultrasonic diagnostic image of high spatial resolution.

Note that in the above described embodiment, the drive circuit 34 for driving the ultrasonic transducer cell 100 is formed separately from the ultrasonic transducer cell 100 and mounted on the FPC 35, but the present invention is not limited to this form.

As described above, it is possible to form the substrate included in the ultrasonic transducer cell according to the present invention into a silicon semiconductor substrate. However, it is possible to monolithically form at least a part of the electronic circuit for driving the ultrasonic transducer cell 100 on the silicon semiconductor substrate. By forming the drive circuit on the substrate 101 in this way, it is possible to eliminate the process for separately mounting the drive circuit and to thereby reduce the number of processes. Further, it is possible to improve the reliability of the electrical connection between the drive circuit and the ultrasonic transducer cell 100.

Second Embodiment

Figure 9:
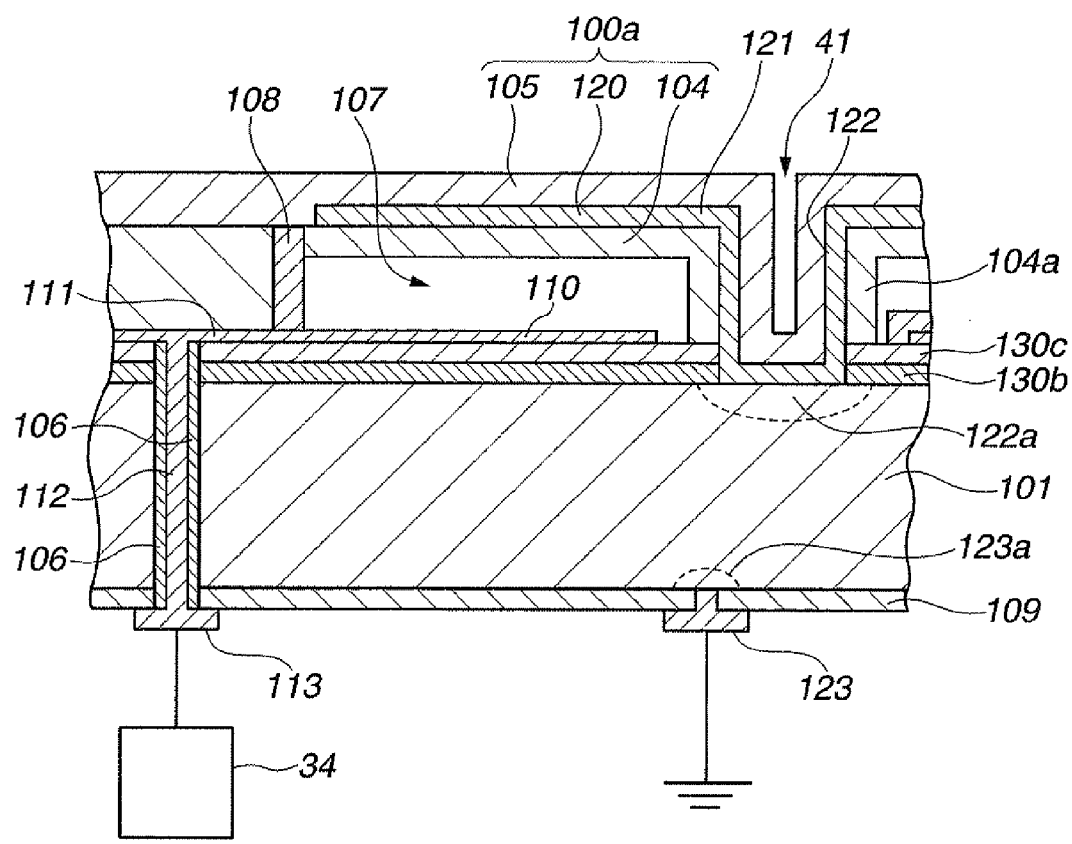
FIG. 9 is a partial cross-sectional view of an ultrasonic transducer cell according to a second embodiment.

In the following, a second embodiment according to the present invention will be described with reference to FIG. 9. FIG. 9 is a partial cross-sectional view of an ultrasonic transducer cell according to the second embodiment. The second embodiment is different from the first embodiment only in the configuration of the charge holding portion. Therefore, in the following, only the difference will be described. Further, components common to the first embodiment are denoted by the same reference numerals and characters, and their description is suitably omitted.

When an electret film made of an inorganic material is used in the charge holding portion, the charges are captured in a defective part of atom bonding, such as a lattice defect and a dangling bond. That is, it is possible to increase the amount of charges held in the electret film by increasing the density of the lattice defect or the dangling bond in the electret film.

Thus, in the present embodiment, the electret film is formed into a multiple layer configuration in which a plurality of electret films are layered. When a plurality of electret films are layered, the electret films of the same kinds may be layered respectively, or a plurality of electret films of different kinds may also be layered. More specifically, an electret film made of a silicon compound may be layered, or an electret film made of a hafnium oxide may be layered. An electret film made of a silicon compound and an electret film made of a hafnium oxide may also be layered. Preferred examples of the silicon compound or the hafnium oxide are as described in the above described first embodiment. The electret film illustrated in FIG. 9 is formed by layering an $SiO_2$ film 130b and an SiN film 130c.

Generally, the dangling bond is present in a material surface in a high density. However, for example, when the material surface is exposed to a gas, the charges held in the dangling bond is neutralized by foreign ions present in the gas. However, as in the present embodiment, when the electret film is formed into a layered configuration, the charges held in the boundary surface between the respective layers are hardly influenced by the foreign ions.

Therefore, according to the present embodiment, by forming the electret film into a layered configuration of a plurality of layers, it is possible to stably hold more charges for a longer period of time, as compared with the case where the electret film is configured by a single layer.

Note that the combination of the materials for configuring the electret film having the layered configuration is not limited to the above described embodiments. For example, the electret film may be configured by a combination of a silicon compound and a hafnium oxide, such as a combination of an $SiO_2$ film and an $HfO_2$ film, a combination of an $HfAl_2O_5$ film and an SiN film, a combination of an $SiO_2$ film and $HfAl_2O_5$ film, or a combination of SiN film and an $HfO_2$ film. In this way, by using the highly insulating silicon compound and hafnium oxide as the electret film, it is possible to fix the charges in a trap of deep level in the electret film. Thereby, it is possible to obtain the electric potential stabilized over a long period of time, and to improve the reliability of the operation of the ultrasonic transducer cell.

The other effects according to the present embodiment are the same as those of the first embodiment, and hence their description is omitted.

Third Embodiment

Figure 10:
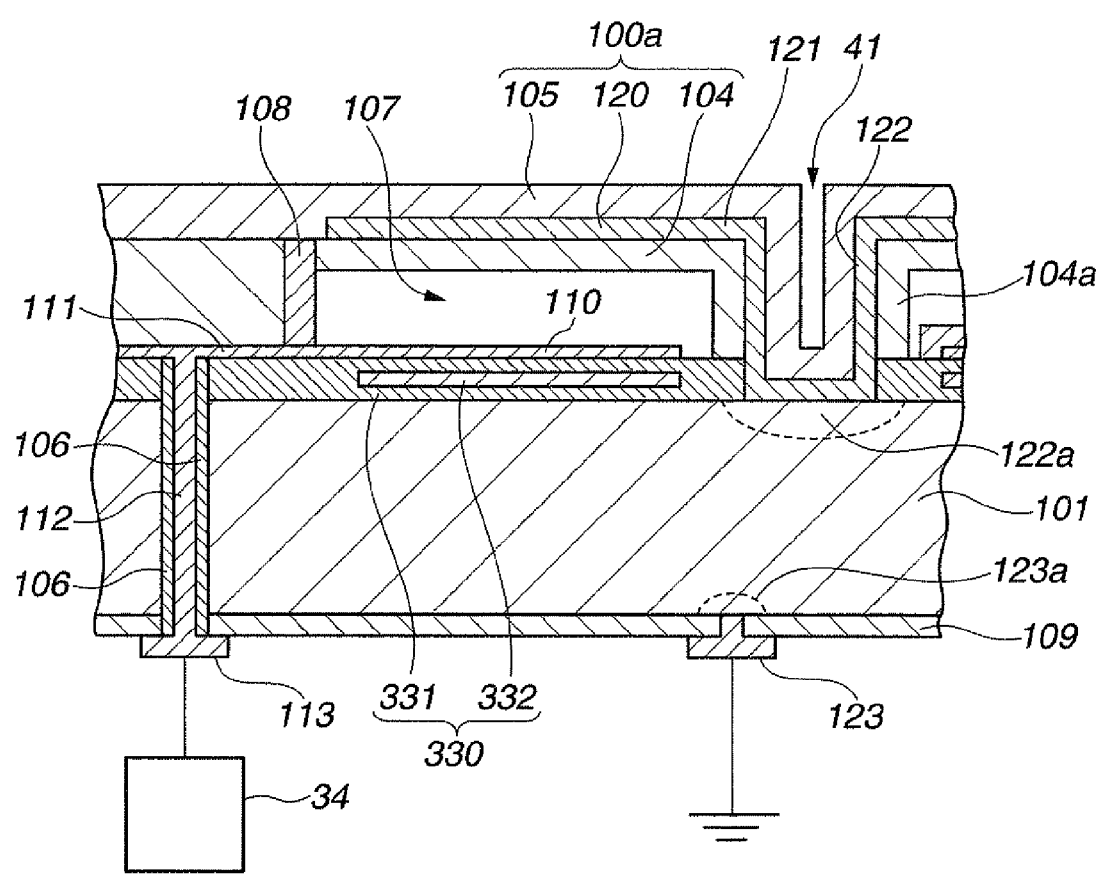
FIG. 10 is a partial cross-sectional view of an ultrasonic transducer cell according to a third embodiment.

In the following, a third embodiment according to the present invention will be described with reference to FIG. 10. FIG. 10 is a partial cross-sectional view of an ultrasonic transducer cell according to the third embodiment. The third embodiment is different from the first embodiment only in the configuration of the electret film. Therefore, in the following, only the difference will be described. Further, components common to the first embodiment are denoted by the same reference numerals and characters, and their description is suitably omitted.

Figure 11:
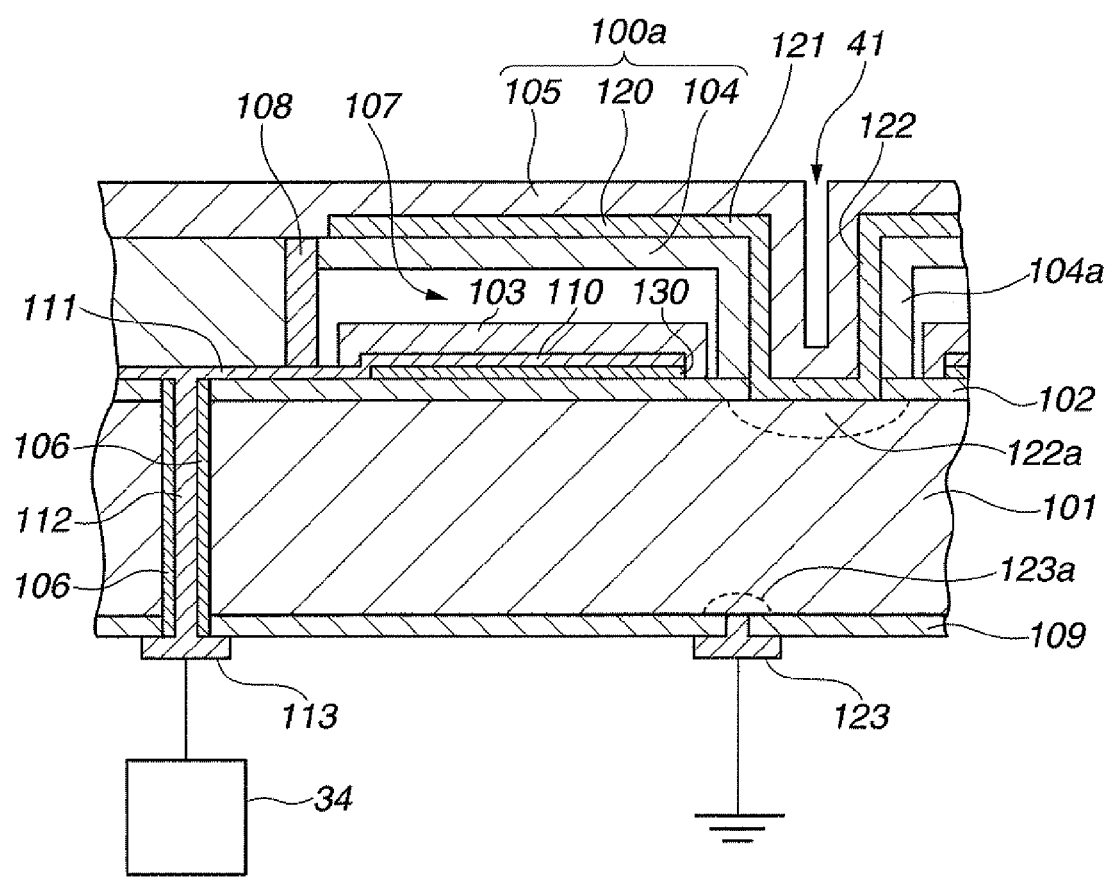
FIG. 11 is a partial cross-sectional view of an ultrasonic transducer cell according to a fourth embodiment.

In the present embodiment, as shown in FIG. 11, an electret film 330 is formed in such a manner that a charge holding film 332 made of a material different from a material of a dielectric film 331 formed on the substrate 101 is embedded in a shape of a float in the dielectric film 331.

The material configuring the charge holding film 332 embedded in the dielectric film 331 is not limited in particular, and for example, there are listed, as the material, a metal such as W, Mo, or Ta, a semiconductor such as a poly-silicon, or an amorphous silicon, or a dielectric film such as $Ta_2O_5$, $TiO_2$, $Al_2O_3$, $ZrO_2$, or $HfO_2$. Also in the present embodiment, similarly to the second embodiment, the electret film is capable of stably holding more charges for a longer period of time, as compared with the case where the electret film is configured by a single layer. Thereby, it is possible to improve the reliability of the operation of the ultrasonic transducer cell.

The other effects according to the present embodiment are the same as those of the first embodiment, and hence their description is omitted.

Fourth Embodiment

Figure 12:
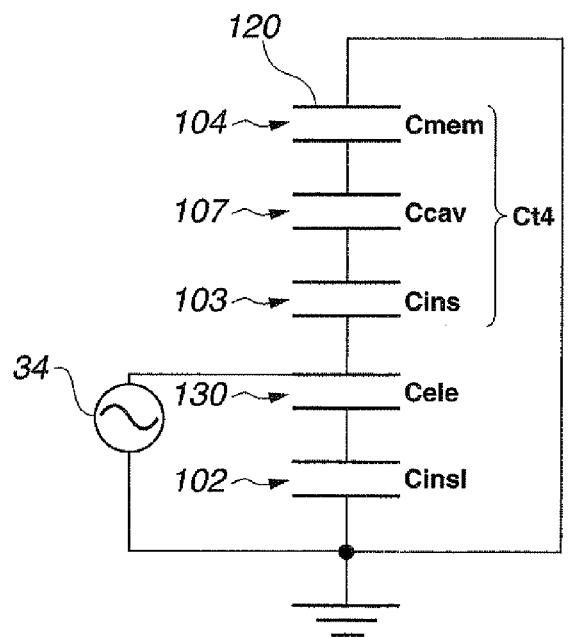
FIG. 12 is an equivalent circuit diagram of the ultrasonic transducer cell according to the fourth embodiment.

In the following, a fourth embodiment according to the present invention will be described with reference to FIG. 11 and FIG. 12. FIG. 11 is a partial cross-sectional view of an ultrasonic transducer cell according to the fourth embodiment. FIG. 12 is an equivalent circuit diagram of the ultrasonic transducer cell according to the fourth embodiment. The fourth embodiment is different from the first embodiment only in the layered configuration of the ultrasonic transducer cell. Therefore, in the following, only the difference will be described. Further, components common to the first embodiment are denoted by the same reference numerals and characters, and their description is suitably omitted.

In the ultrasonic transducer cell according to the present embodiment, a lower protective film 103 having an electrical insulating property is formed so as to be in contact with the upper surface of the lower electrode 110, and to cover the lower electrode 110. The material for configuring the lower protective film 103 is not limited in particular, and there are listed, as the material, a silicon nitride, nitride hafnium (HfN), or hafnium oxide nitride (HfON). In particular, when HfN or HfON is used, it is possible to obtain a high density film and to thereby reduce the thickness of the film. As a result, it is possible to suppress the influence of providing the lower protective film 103, on the cavity 107 and on the distance between the upper and lower electrodes. Therefore, it is possible to suppress to a minimum the amount of decrease in the composite capacitance Ct4 between the upper electrode 120 and the lower electrode 111, which amount of decrease is caused by providing the lower protective film 103.

The method for forming the lower protective film 103 is not limited in particular, and for example, the lower protective film 103 can be formed by the plasma CVD method.

As in the present embodiment, by providing the lower protective film 103 also on the lower electrode 110, it is possible to prevent the lower electrode 110 from being damaged by the sacrificial layer etching, the heat treatment, and the like in the manufacturing process of the ultrasonic transducer cell, which process is performed after the lower electrode 110 is formed.

Therefore, according to the present embodiment, it is possible to form the film on the lower electrode 110 in a uniform quality and thickness in all the ultrasonic transducer cells configuring the ultrasonic transducer array 31. Consequently, it is possible to uniform the characteristics, such as the frequency and sound pressure of transmitted ultrasounds of each ultrasonic transducer cell and to thereby obtain an ultrasonic diagnostic image of higher spatial resolution.

The other effects according to the present embodiment are the same as those of the first embodiment, and hence their description is omitted.

Fifth Embodiment

Figure 13:
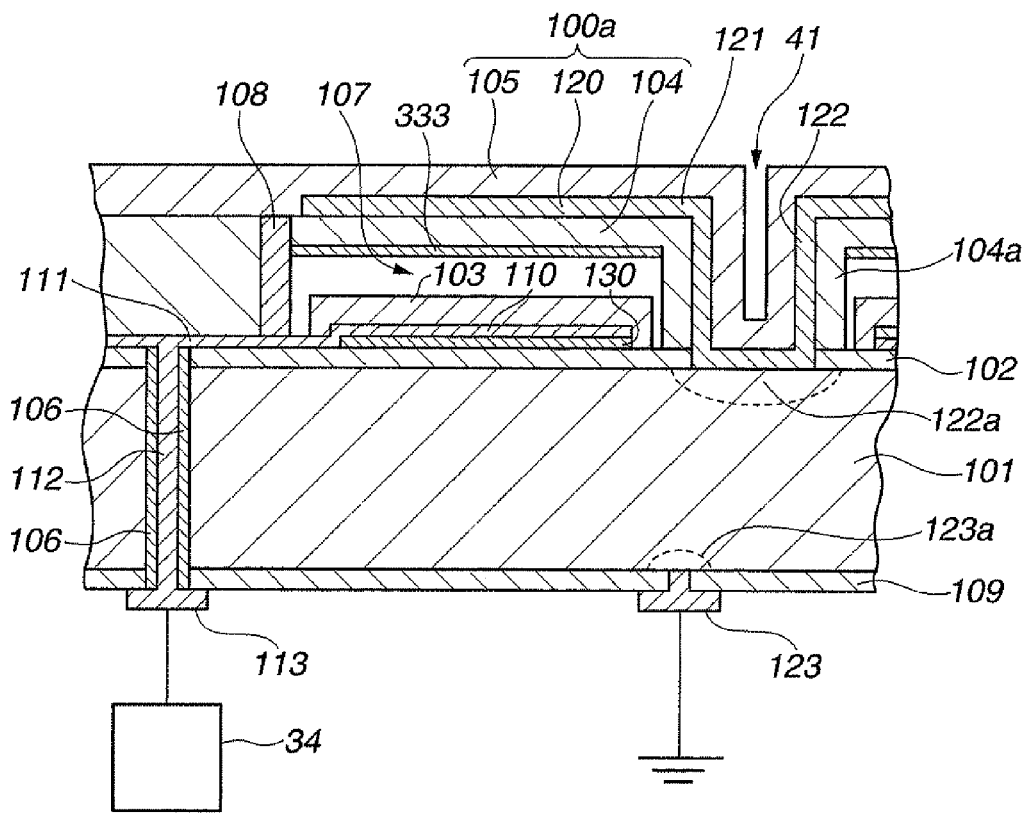
FIG. 13 is a partial cross-sectional view of an ultrasonic transducer cell according to a fifth embodiment.
Figure 14:
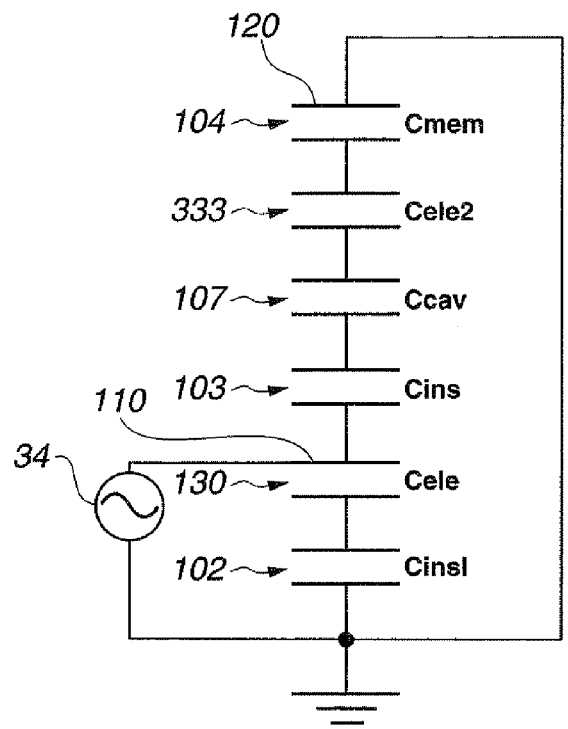
FIG. 14 is an equivalent circuit diagram of the ultrasonic transducer cell according to the fifth embodiment.

In the following, a fifth embodiment according to the present invention will be described with reference to FIG. 13 and FIG. 14. FIG. 13 is a partial cross-sectional view of an ultrasonic transducer cell according to the fifth embodiment. FIG. 14 is an equivalent circuit diagram of the ultrasonic transducer cell according to the fifth embodiment. The fifth embodiment is different from the fourth embodiment only in the arrangement and the number of the electret films. Therefore, in the following, only the difference will be described. Further, components common to the first embodiment are denoted by the same reference numerals and characters, and their description is suitably omitted.

In the ultrasonic transducer cell according to present embodiment, in addition to the charge holding portion 130 arranged as the lower layer of the lower electrode 110, another second electret film 333 is arranged between the lower electrode 110 and the upper electrode 120. More specifically, in the present embodiment, it is possible to arrange the second electret film 333 in a portion between the cavity 107 and the lower electrode 110, a portion between the second insulating film 104 and the cavity 107, or a portion between the upper electrode 120 and the second insulating film 104. In FIG. 13, the second electret film 333 is provided between the cavity 107 and the second insulating film 104. Here, the polarity direction of polarization of the second electret film 333 is set so as not to cancel the charges held in the charge holding portion 130.

In the present embodiment, it is possible to hold more charges by providing the second electret film 333, and to thereby further increase the potential difference between the lower electrode 111 and the upper electrode 120. That is, it is possible to obtain a state electrically equivalent to the state where the DC bias voltage applied between the lower electrode 110 and the upper electrode 120 is further increased, and to thereby further improve the transmission and reception sensitivity of ultrasounds of the ultrasonic transducer cell.

The other effects according to the present embodiment are the same as those of the fourth embodiment, and hence their description is omitted.

Sixth Embodiment

Figure 15:
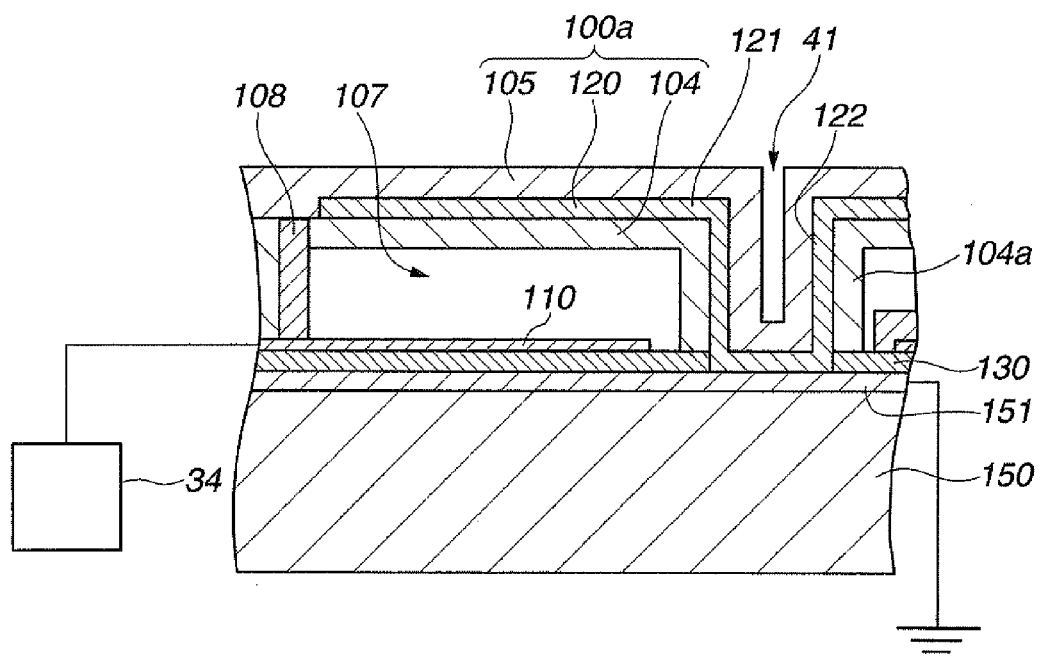
FIG. 15 is a partial cross-sectional view of an ultrasonic transducer cell according to a sixth embodiment.
Figure 16:
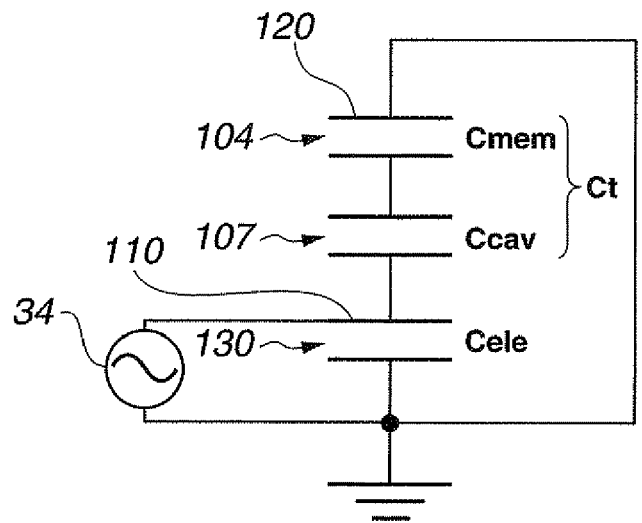
FIG. 16 is an equivalent circuit diagram of the ultrasonic transducer cell according to the sixth embodiment.
Figure 17:
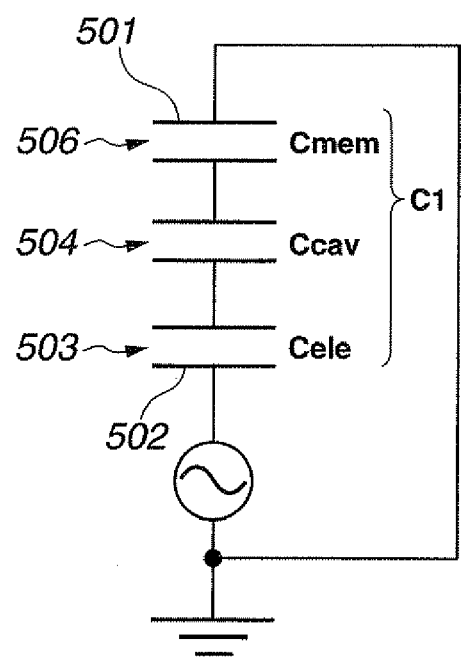
FIG. 17 is an equivalent circuit diagram of a conventional capacitive transducer.

In the following, a sixth embodiment according to the present invention will be described with reference to FIG. 15 and FIG. 16. FIG. 15 is a partial cross-sectional view of an ultrasonic transducer cell according to the sixth embodiment. FIG. 16 is an equivalent circuit diagram of the ultrasonic transducer cell according to the sixth embodiment. The sixth embodiment is different from the first embodiment only in the material of the substrate on which the ultrasonic transducer cell is formed. Therefore, in the following, only the difference will be described. Further, components common to the first embodiment are denoted by the same reference numerals and characters, and their description is suitably omitted.

In the present embodiment, a substrate 150 is an insulating substrate configured by an insulating material, and a grounding conductive layer 151 set to the ground potential is arranged between the substrate 150 and the charge holding portion 130. The insulating substrate is as described in the above described first embodiment.

The same configuration as the ultrasonic transducer cell 100 of the first embodiment is layered on the grounding conductive layer 151. Further, the ultrasonic transducer cell according to the present embodiment is equivalent to an ultrasonic transducer cell obtained by replacing the substrate 101 configured by a conductive material with the grounding conductive layer 151, and is represented by an equivalent circuit as shown in FIG. 16.

The method for forming the grounding conductive layer 151 is not limited in particular, and it is possible to use sputtering as the method.

The material configuring the grounding conductive layer 151 is not limited in particular, and it is possible to use a conventionally known conductive material. As the material, there are listed, for example, Cr, Ni, Cu, Ti, Sn, Pt, Au, W, Mo, Ta or the like. Note that the grounding conductive layer 151 may have a multilayer configuration formed by layering a plurality of kinds of conductive materials. For example, the grounding conductive layer may be configured by two metallic layers, the lower side of which (the side in contact with the substrate 150) is made of one of Cr, Ni, Cu, Ti and Sn, and the upper side of which is made of one of Pt, Au, W, Mo and Ta.

The ultrasonic transducer cell according to the present embodiment can be electrically connected to the wiring pattern of the FPC by a wire bonding or the like, after the rear surface side of the insulating substrate 150 is fixed on the FPC by an adhesive or the like. Thereby, the grounding conductive layer 151 and the lower electrode 110 are electrically connected to the ground potential and the control circuit 34, respectively.

According to the present embodiment, as compared with the case where the ultrasonic transducer cell is formed on the conductive substrate, it is possible to suppress the parasitic capacitance from being generated at the time when the conductive substrate is used as the wiring, and to thereby more efficiently perform the drive control of the ultrasonic transducer cell.

Note that the present invention is not limited to the above described embodiments, but may be suitably modified without departing from the scope and spirit of the invention read from the appended claims and the whole specification. An ultrasonic transducer cell, an ultrasonic transducer element, an ultrasonic transducer array, and an ultrasonic diagnostic apparatus, which are subjected to such modification, are also included within the scope of the present invention.

For example, the above described ultrasonic endoscope is described as an endoscope configured to perform the electronic radial scanning and the electronic sector scanning. However, the scanning system is not limited to these, and a liner scanning system, a convex scanning system or the like may also be adopted. Further, the ultrasonic transmission and reception portion may be configured as one dimensional array in which a plurality of ultrasonic transducer elements are one-dimensionally arranged. Further, the present invention is also applicable to an ultrasonic endoscope of a mechanical scanning type. Thus, it is possible to apply the present invention not only to an ultrasonic endoscope configured by arranging the above described ultrasonic transducer elements in an array form, but also to an ultrasonic endoscope using a single ultrasonic transducer element.

Further, the present invention is not limited to an endoscope provided with an ultrasonic transmission and reception portion at the distal end of the endoscope, but belongs to a technical field including all of the so-called ultrasonic probes which are introduced into the inside of the body, regardless of a wired type or a radio type.

What is claimed is:

1. An ultrasonic transducer cell comprising:
   a substrate;
   a lower electrode used to input and output a signal;
   a vibration membrane arranged on a first side of the lower electrode, the first side of the lower electrode being opposite to a second side of the lower electrode on which the substrate is arranged, the vibration member being separated from the lower electrode with a cavity and configured to include an insulating film and an upper electrode; and
   a charge holding portion formed by charging an insulating material,
   wherein the charge holding portion is arranged between the substrate and the lower electrode.

2. The ultrasonic transducer cell according to claim 1, wherein the charge holding portion is an electret film.

3. The ultrasonic transducer cell according to claim 2, wherein the electret film is a single-layer film or a multi-layer film, and is made of a silicon compound.

4. The ultrasonic transducer cell according to claim 2, wherein the electret film is a single-layer film or a multi-layer film, and is made of hafnium oxide.

5. The ultrasonic transducer cell according to claim 2, wherein the electret film is formed by layering a film made of a silicon compound and a film made of hafnium oxide.

6. The ultrasonic transducer cell according to claim 2, wherein a second electret film is provided between the lower electrode and the upper electrode.

7. The ultrasonic transducer cell according to claim 1, wherein the substrate is an insulating substrate configured by an electrically insulating material, and wherein a grounding conductive film having a conductive property and set to the ground potential is provided between the insulating substrate and the charge holding portion.

8. The ultrasonic transducer cell according to claim 2, wherein the substrate is an insulating substrate configured by an electrically insulating material, and wherein a grounding conductive film having a conductive property and set to the ground potential is provided between the insulating substrate and the charge holding portion.

9. The ultrasonic transducer cell according to claim 1, wherein the substrate is a conductive substrate configured by a conductive material, and the conductive substrate is set to the ground potential.

10. The ultrasonic transducer cell according to claim 2, wherein the substrate is a conductive substrate configured by a conductive material, and the conductive substrate is set to the ground potential.

11. The ultrasonic transducer cell according to claim 10, wherein the conductive substrate is made of a silicon semiconductor.

12. The ultrasonic transducer cell according to claim 9, wherein the conductive substrate is made of a silicon semiconductor.

13. The ultrasonic transducer cell according to claim 1, wherein an electrically insulating protective film is provided between the lower electrode and the cavity.

14. The ultrasonic transducer cell according to claim 2, wherein an electrically insulating protective film is provided between the lower electrode and the cavity.

15. An ultrasonic transducer element comprising the ultrasonic transducer cell according to claim 1.

16. An ultrasonic transducer array comprising the ultrasonic transducer element according to claim 15.

17. An ultrasonic diagnostic apparatus comprising the ultrasonic transducer array according to claim 16.

* * * * *